United States Patent [19]

Toya et al.

[11] Patent Number: 4,483,270
[45] Date of Patent: Nov. 20, 1984

[54] APPARATUS FOR EMBEDDING BIOLOGICAL SPECIMENS IN PARAFFIN OR THE LIKE PREPARATORY TO MICROSCOPICAL EXAMINATION

[75] Inventors: Matsumi Toya; Toshiyasu Takeuchi, both of Nagano, Japan

[73] Assignee: Kabushiki Kaisha Tiyoda Seisakusho, Nagano, Japan

[21] Appl. No.: 426,573

[22] Filed: Sep. 29, 1982

Related U.S. Application Data

[63] Continuation-in-part of Ser. No. 413,312, Aug. 31, 1982, abandoned.

[30] Foreign Application Priority Data

Sep. 3, 1981 [JP] Japan ............................ 56-130358[U]
Sep. 3, 1981 [JP] Japan ............................ 56-130359[U]
Sep. 3, 1981 [JP] Japan ................................ 56-137840

[51] Int. Cl.³ ............................ B05C 3/00; B08B 3/00
[52] U.S. Cl. ..................................... 118/694; 118/421; 118/429; 118/702; 134/103; 55/255; 251/300
[58] Field of Search ............... 118/692, 693, 694, 429, 118/421, 610, 61, 702; 134/102, 103; 137/625.11, 625.19; 55/255; 251/300

[56] References Cited

U.S. PATENT DOCUMENTS

3,773,078 11/1973 Suntheimer .................... 137/625.11
3,844,748 10/1974 Lanier ................................. 55/255
3,854,440 12/1974 Astle .................................. 118/429
3,892,197 7/1975 Kinney et al. ..................... 118/429
3,998,426 12/1976 Isbester ............................. 251/300
4,141,312 2/1979 Louder et al. ..................... 118/702

Primary Examiner—John E. Kittle
Assistant Examiner—James J. Seidleck
Attorney, Agent, or Firm—Ladas & Parry

[57] ABSTRACT

An apparatus for automatically pretreating and paraffining biological specimens in a single vessel for the preparation of specimen blocks to be microtomed into thin slices for microscopical study. A rotary selector valve assembly with a built-in gate valve placed a plurality of reagent vessels, containing various reagents including molten paraffin, in and out of communication with the processing vessel in a prescribed sequence. An air pump coacts with directional control valves to evacuate the processing vessel for drawing the successive reagents into same via the rotary selector valve assembly and to deliver gas under pressure into the vessel for the discharge of the reagents therefrom back into the respective reagent vessels. For automating the apparatus a level sensor is provided to the processing vessel in order to close the gate valve and to set the pump out of operation whenever a reagent is drawn into the processing vessel to a predetermined level. Also included are a first pressure switch for opening the gate valve in response to the delivery of the pressurized gas from the pump into the processing vessel, and a second pressure switch for stopping the pump and causing the selector valve assembly to communicate the processing vessel with the next reagent vessel in response to a pressure drop upon complete discharge of the reagent from the processing vessel.

9 Claims, 12 Drawing Figures

APPARATUS FOR EMBEDDING BIOLOGICAL SPECIMENS IN PARAFFIN OR THE LIKE PREPARATORY TO MICROSCOPICAL EXAMINATION

This application is a continuation-in-part of our copending application Ser. No. 413,312 filed Aug. 13, 1982, now abandoned.

BACKGROUND OF THE INVENTION

This invention relates to an apparatus for pretreating biological specimens, such as pieces of tissue, with a variety of reagents and finally embedding them in paraffin or like substance, thereby preparing blocks to be microtomed into thin slices, known micro-logically as sections, for microscopical study.

Of several known types of microscope slide commonly used today, sections are perhaps the best suited for detailed study of the tissues or cells of organic structures. Direct hand slicing is possible for some structures. But most biological specimens do not lend themselves to such treatment but must be impregnated with, and embedded in, a substance that sections well. The preparation of paraffin blocks requires such pretreatments of the specimens as degreasing, dehydration, and fixation of tissue by immersion in alcohol, formalin, and xylene, among other reagents.

Apparatus has been suggested and used for pretreating biological specimens in various ways and embedding the pretreated specimens in paraffin, all in a single vessel. The apparatus comprises a required number of reagent vessels containing molten paraffin and other reagents. A rotary selector valve coacts with a gate valve to communicate the reagent vessels with the single processing vessel in a prescribed sequence, the latter vessel having biological specimens placed therein. The processing vessel draws the reagents in from the successive reagent vessels by being evacuated with an air pump and discharges them either by admitting atmospheric air or by being pressurized with the pump.

The known apparatus has several drawbacks. The first of these concerns the supply and discharge of the reagents to and from the processing vessel. For reagent supply the usual practice has been to maintain the processing vessel in partial vacuum for a length of time required for the complete contents of each reagent vessel to flow into the processing vessel, plus some extra period. This practice is objectionable because the reagent vessels may contain less than required amounts of reagents. The prior art apparatus has no means for sensing the undersupply of the reagents, possibly resulting in the exposure of the specimens in the processing vessel to air for a prolonged length of time and so making them unsuitable for microscopical investigation.

For reagent discharge, too, the conventional practice has been to deliver air under pressure into the processing vessel for a period of time required for the full withdrawal of the reagent therefrom, plus some added time. During this additional period, then, the pressurized air flows into the reagent vessel to which the reagent has been recovered from the processing vessel. The influx of the pressurized air into the filled reagent vessel causes the bubbling of the recovered reagent and the consequent evaporation of the solution and the liberation of noxious gases.

It must also be taken into consideration that the extra periods during which the processing vessel is held evacuated and pressurized for reagent supply and discharge sum up to a considerable length of time since the reagent vessels number as many as fourteen or so. Such waste of time should of course be avoided.

Another drawback in the prior art is that, as far as the applicant is aware, no measure has been taken against pollution of the working environment. The reagents for the processing of organic specimens include chloroform, xylene, alcohol, etc., which emit gases that are toxic when inhaled. The apparatus is usually installed in a closed space and operates for an extended period of time, during which the concentrations of the noted gases may increase to fatal degrees.

Also, in the known apparatus, trouble has been liable to occur from the directional control valve for selectively communicating the processing vessel with the pump and with atmosphere. In the event of the malfunctioning of this valve the processing vessel may fail to discharge a reagent and may still be charged with another. Overflowing from the vessel, the blended reagents will then enter and destroy the pump. Moreover, if a trouble occurs to the rotary selector valve, a reagent drained from the processing vessel may be directed into a wrong reagent vessel thereby causing overflow therefrom. The rotary valve as heretofore constructed has been unsatisfactory in respects of durability and resistance to heat and chemicals.

SUMMARY OF THE INVENTION

It is an object to provide an apparatus for pretreating biological specimens in which the supply and discharge of reagent can be made speedly and safely during the operation.

Another object of the invention is to eliminate the pollution of the working environment with the exhaust gases of the apparatus.

A further object of the invention is to provide a rotary selector valve assembly of improved construction and performance characteristics for use in the micrological apparatus.

Stated in its perhaps broadest aspect, the invention provides apparatus comprising a hermetically closed processing vessel for receiving a biological specimen to be pretreated and embedded in a desired substance such as paraffin, and a plurality of reagent vessels for containing reagents, including paraffin or the like, for processing the specimen in the processing vessel. Selector valve means placed the reagent vessels in and out of communication with the processing vessel in a prescribed sequence. As dictated by directional control valve means, an air pump operates to evacuate the processing vessel for causing same to draw the successive reagents from the reagent vessels via the selector valve means, and to pressurize the processing vessel for the discharge of the reagents therefrom back to the original reagent vessels. Provided for the automatic, fail-safe operation of the apparatus are a level sensor and pressure switch means. The level sensor acts to set the pump out of operation, and to cause the selector valve means to block communication between the processing vessel and any of the reagent vessels, when the reagent from that reagent vessel is drawn into the processing vessel to a predetermined level. The pressure switch means, on the other hand, operates to cause the selector valve means to reestablish communication between the processing vessel and that one of the reagent vessels from which the reagent has been drawn into the processing vessel, in response to the pressure of the pressurized gas delivered from the pump into the processing vessel for the discharge of the reagent therefrom. The pressure switch means also responds to a pressure drop upon complete discharge of the reagent from the processing vessel in order to set the pump out of operation.

The above and other objects, features and advantages of this invention and the manner of attaining them will become more apparent, and the invention itself will be best understood, from a study of the following description and appended claims, with reference to the attached drawings.

DETAILED DESCRIPTION OF THE INVENTION

Figure 1:
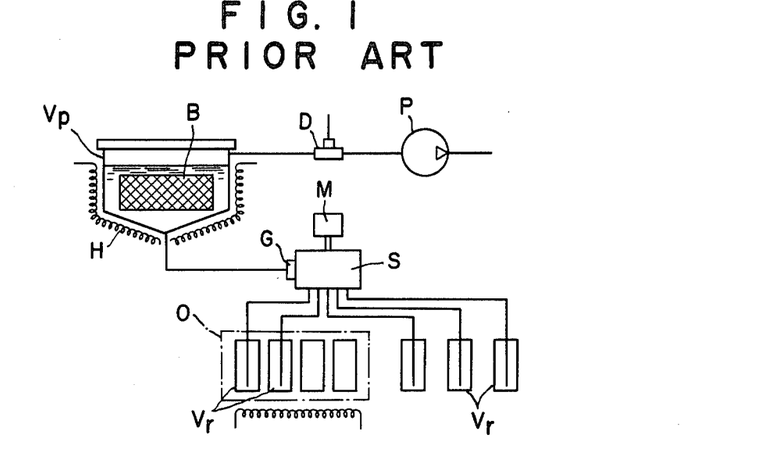
FIG. 1 is a diagrammatic representation of prior art apparatus believed to be closest to that according to the invention.

The prior art apparatus of FIG. 1 has a processing vessel Vp having placed therein a box B of permeable material containing a specimen or specimens to be processed. The processing vessel Vp has an electric heater H for heating paraffin and other reagents that must be heated or held heated in use. The processing vessel communicates with a gate valve G and thence with a rotary selector valve S driven by an electric motor M. The selector valve S communicates with a required number of reagent vessels Vr containing paraffin and other reagents. Of these reagent vessels those containing paraffin and other reagents that must be heated for use, such as formalin, are housed in a thermostatically controlled over O. A three-way directional control valve D selectively communicates the processing vessel Vp with an air pump P and with atomosphere.

In the use of this prior art apparatus the box B containing a biological specimen or specimens is placed in the processing vessel Vp. Then the processing vessel is closed hermetically. Then the rotary selector valve S is motor-driven to establish communication between gate valve G and one of the reagent vessels Vr containing the reagent to be first introduced into the processing vessel Vp. Thereafter the gate valve G is opened, and the pump P is set into operation to evacuate the processing vessel Vp. The evacuated processing vessel draws the first required reagent from its vessel via the selector valve S and gate valve G, with the result that the specimen box B becomes immersed in the reagent. Then the gate valve G is closed, and the pump P is set out of operation.

The reagent must be withdrawn from the processing vessel Vp back into the initial vessel Vr after treatment of the specimen or specimens for a prescribed length of time, which may be from one to two hours. To this end the three-way directional control valve D is actuated to communicate the processing vessel Vp with atomosphere, thereby admitting atmospheric air into the vessel, if the reagent vessels Vr are disposed lower than the processing vessel Vp. If not, the output side of the pump is communicated with the processing vessel to force air into the vessel. As the gate valve G is opened, the reagent is drained from the processing vessel and flows back into its own reagent vessel either under atmospheric pressure or under pump output pressure. Then the selector valve S is actuated to communicate the second required reagent vessel with the processing vessel. Thereafter the same cycle of operation is repeated until finally the specimen or specimens are impregnated with and embedded in paraffin.

The objections to this prior art apparatus are as set forth previously. How the present invention overcomes all these objections will become apparent from the following description of a preferred embodiment.

Figure 2:
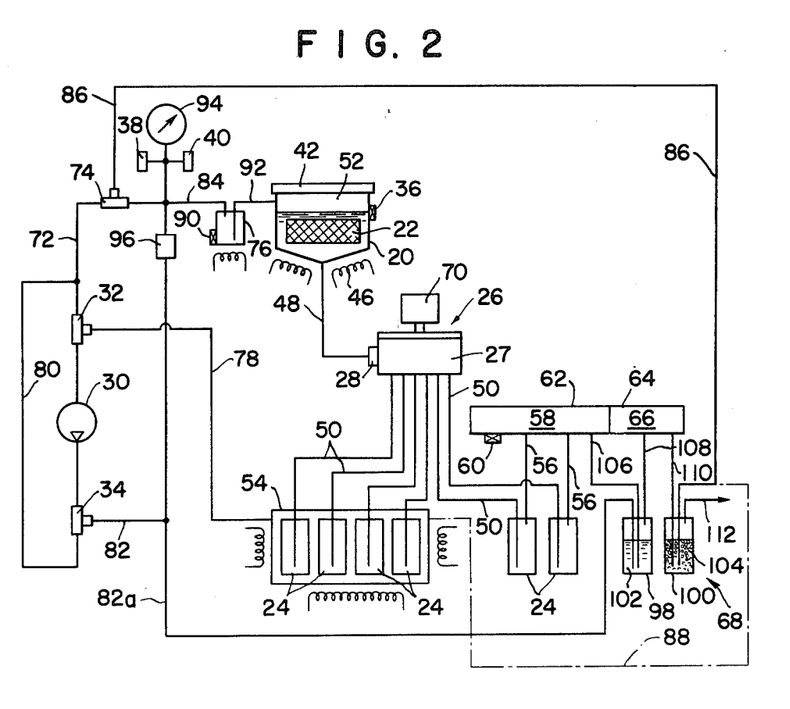
FIG. 2 is a diagrammatic representation of a preferred form of the apparatus for pretreating embedding biological specimens in paraffin or the like in accordance with the principles of the present invention.

With reference now directed to FIG. 2 the illustrated apparatus according to the invention broadly comprises:

1. a processing vessel 20 for receiving a biological specimen or specimens contained in a box 22 of permeable material;

2. any required number of reagent vessels 24 containing various reagents including paraffin or an equivalent substance;

3. a rotary selector valve assembly 26 comprising a selector valve 27 proper and a gate valve 28 for placing the reagent vessels 24 in and out of communication with the processing vessel 20 in a prescribed sequence;

4. an air pump 30 under the control of three-way directional control valves 32 and 34 for selectively exhausting and pressurizing the processing vessel 20 for the introduction and discharge of the successive reagents to and from same;

5. a level sensor 36 provided to the processing vessel 20 and controlling the gate valve 28 and pump 30; and 6. first and second pressure switches 38 and 40 responsive to gas pressures between processing vessel 20 and pump 30 and also controlling the gate valve 28 and pump 30.

The processing vessel 20 has an open top hermetically closed with a lid 42. This lid is to be opened for placing the specimen box 22 in the processing vessel and for withdrawing the box upon completion of the required processing. An electric heater 46 is provided to the processing vessel 20 as in the prior art. The processing vessel has its bottom coupled to a conduit 48 leading to the gate valve 28 provided on the rotary selector valve assembly 26, for receiving the successive reagents from the reagent vessels 24 and returning the reagents back to the respective reagent vessels.

All hermetically closed, the reagent vessels 24 separately contain a fixative solution such as formalin, a dehydrating and degreasing agent such as alcohol, a solvent such as xylene, a substance such as paraffin with and in which the specimen or specimens in the processing vessel 20 are to be impregnated and embedded, etc. Although FIG. 2 shows only six reagent vessels 24, in practice there may be used, for instance, fourteen such vessels for the usual processing of biological specimens. All the reagent vessels 24 communicate with the inlet ports of the rotary selector valve 27 via respective conduits 50 for succcessive communication with the processing vessel 20 via the gate valve 28. The capacities of the reagent vessels 24 are determined in relation to that of the processing vessel 20. When the full contents of each reagent vessel are drawn into the processing vessel, the specimen box 22 must be thoroughly immersed in the reagent, with some headspace 52 left in the vessel.

It will be seen that some of the reagent vessels 24 are housed in a thermostatically controlled oven 54. The vessels in the oven include two containing molten paraffin and others containing reagents such as formalin that must be heated for use. In the use of these reagents that must be held at elevated temperatures, the processing vessel is heated by the heater 46, and the rotary selector valve assembly 26 and the conduits 48 and 50 are also heated as required by means not shown in this figure. The other reagent vessels 24 are shown to have their top ends coupled to conduits 56 leading to an overflow vessel 58. This overflow vessel has an ultrasonic sensor 60 for detecting the overflow of the reagents from the reagent vessels 24. In the illustrated embodiment the overflow vessel 58 forms a part of a vessel 62. A partition 64 divides the vessel 62 into two sections, one serving as the overflow vessel 58 and the other as an intermediate vessel 66 of an exhaust scrubber 68 to be detailed presently.

The rotary selector valve assembly 26 comprises the selector valve 27 driven by an electric motor 70 for communicating the successive reagent vessels 24 with the processing vessel 20, and the gate valve 28 for the on-off control of communication between each selected reagent vessel and the processing vessel. The detailed construction of this rotary selector valve assembly will be later explained with reference to FIGS. 5 to 11.

The pump 30 performs the dual function of evacuating the processing vessel 20 for the introduction of the successive reagents from the reagent vessels 24 and of delivering gas under pressure to the processing vessel for the discharge of the reagents therefrom. The performance of this dual function by the pump 30 requires the aid of the two three-way directional control valves 32 and 34. The first three-way valve 32 has:

1. a first inlet port open to a conduit 72 leading to the processing vessel 20 via an additional three-way directional control valve 74 and an overflow vessel 76;

2. a second inlet port open to a conduit 78 leading to the oven 54; and 3. an outlet port in direct communication with the inlet of the pump 30.

The second three-way valve 34 has:

1. an inlet port in direct communication with the outlet of the pump 30;

2. a first outlet port open to a conduit 80 connected to the conduit 72; and 3. a second outlet port open to a conduit 82 leading to the exhaust scrubber 68.

The third mentioned three-way valve 74 normally holds the conduit 72 in communication with a conduit 84 leading to the overflow vessel 76. The valve 74 is required to only establish communication between the conduit 72 and a conduit 86 which is open to atmosphere via the exhaust scrubber 68. The oven 54 has an air intake port which can be left open to atmosphere or, as required, communicated with the conduit 86 via a phantom conduit 88.

It will have been seen from the foregoing that the three-way valves 32 and 34 can cause the pump 30 both to evacuate the processing vessel 20, directing the exhaust gases toward the exhaust scrubber 68, and to pressurize the processing vessel by drawing air from the oven 54.

The level sensor 36 on the processing vessel 20 can be of the known type operating ultrasonically to detect the inflow of any reagent into the vessel to a proper level. Thereupon the level sensor produces an electric output for closing the gate valve 28 and stopping the pump 30. Another ultrasonic level sensor 90 is provided to the overflow vessel 76. A conduit 92 communicating the overflow vessel with the processing vessel 20 opens to the headspace 52 of the latter. Consequently, in the event of liquid oversupply to the processing vessel, the liquid overflows therefrom into the overflow vessel. The level sensor 90 senses the overflow of the liquid from the processing vessel and puts out an electric signal.

The pressure switches 38 and 40, as well as a pressure meter 94, are connected in constant communication with the conduit 84 between three-way valve 74 and overflow vessel 76. The first pressure switch 38 responds to a predetermined pressure (e.g. 0.35 atm.) at which the pump 30 delivers gas toward the processing vessel 20, in order to cause the gate valve 28 to open. The second pressure switch 40 responds to a pressure drop (e.g. 0.1 atm.) upon complete discharge of the reagent from the processing vessel 20, in order to stop the pump 30 and to energize the motor 70 of the rotary selector valve assembly 26 for causing the selector valve 27 to communicate the next reagent vessel 24 with the processing vessel 20. The pressures to which the pressure switches 38 and 40 respond may be suitably determined in consideration of the particular design of the apparatus and the displacement of the pump 30 in use. Connected between the conduits 82 and 84, a relief valve 96 functions to bleed off pressures in excess of the one at which the first pressure switch 38 operates. It will be understood that, instead of the two pressure switches 38 and 40, there could be used a single switch which is set by the pump output pressure and reset by the reduced pressure.

The exhaust scrubber 68 comprises a water vessel 98 and an adsorbent vessel 100, in addition to the aforesaid intermediate vessel 66. The water vessel 98 contains water 102 to a level less than its full capacity whereas the absorbent vessel 100 contains an adsorbent material such as activated carbon 104, also to a level less than its full capacity. The conduit 82 leading from the three-way valve 34 and the relief valve 96, and a conduit 106 leading from the overflow vessel 58, both extend into the water vessel 98 and have thier extremities held sufficiently below the level of the water 102 therein. The headspace of the water vessel 98 communicates with the intermediate vessel 66 via a conduit 108. The intermediate vessel communicates, in turn, with the adsorbent vessel 100 via a conduit 110 having one of its extremities buried deep into the activated carbon 104. The headspace of the adsorbent vessel 100 is open to atmosphere via a conduit 112. The conduit 86 leading to the three-way valve 74 also has one of its extremities buried deep into the activated carbon 104 in the adsorbent vessel 100.

Such being the organization of the micrological apparatus according to the invention, the first three-way valve 32 may be operated to communicate the inlet side of the pump 30 with the processing vessel 20, and the second three-way valve 34 may be operated to communicate the outlet side of the pump with the exhaust scrubber 68, for evacuating the processing vessel. The pump 30 when set into operation will draw air from the processing vessel 20 via the overflow vessel 76, third three-way valve 74, and first three-way valve 32. The air will be sent via the valve 34, conduits 82 and 82a to the water vessel 98 and exhausted to atmosphere after being scrubbed by the water 102 in the water vessel 98 and the activated carbon 104 in the adsorbent vessel 100.

Thus, as in the prior art apparatus of FIG. 1, the reagents in the reagent vessels 24 can be successively introduced into the processing vessel 20 under the control of the rotary selector valve assembly 26. When each reagent flows into the processing vessel 20 to the predetermined level, the level sensor 36 functions in accordance with the invention to close the gate valve 28 and to set the pump 30 out of operation.

The illustrated embodiment provides for two methods of discharging the reagent from the processing vessel 20 upon completion of the treatment of the specimen or specimens therein. One of the methods presupposes that the reagent vessels 24 are disposed below the processing vessel 20. The third three-way valve 74 is activated to admit atmospheric air into the processing vessel via the adsorbent vessel 100 of the exhaust scrubber 68 and the overflow vessel 76. The atmospheric pressure in the processing vessel 20 will force the reagent down to its own vessel 24 via the rotary selector valve assembly 26.

An alternative method is available if the reagent vessels 24 are on a level with, or even above, the processing vessel 20. In these cases the first 32 and second 34 three-way valves are operated to communicate the inlet side of the pump 30 with the oven 54 via the conduit 78, and its outlet side with the processing vessel 20 via the conduits 80 and 72, the third three-way valve 74, the conduit 84, the overflow vessel 76 and the conduit 92. Simultaneously set into motion, the pump 30 will force the pressurized gas, derived from the oven 24, into the processing vessel 20. The pump output pressure activates the first pressure switch 38, causing same to open the gate valve 28. Thus is the reagent withdrawn from the processing vessel back to the initial reagent vessel 24.

Upon complete discharge of the reagent from the processing vessel 20, the pressure in the conduit 84 will drop rapidly. The second pressure switch 40 responds to this reduced pressure to stop the pump 30 and to cause energization of the motor 70 of the rotary selector valve 27 thereby causing the valve to place the next reagent vessel in communication with the processing vessel.

It should be appreciated that the second pressure switch 40 functions to stop the pump immediately upon completion of reagent withdrawal from the processing vessel. This serves to prevent the bubbling of the recovered reagents in the reagent vessels by prolonged pumping and the consequent evaporation of the reagents and emission of noxious gases. Further, since the second pressure switch 40 also works to cause the rotary selector valve 27 to communicate the next reagent vessel with the processing vessel immediately upon complete withdrawal of each reagent from the latter, no time is wasted in transition from one treatment of the specimen or specimens to the next.

In the use of the apparatus it is important that the level sensor 36 on the processing vessel 20 be positioned on the level to which the vessel is to be charged with each reagent. If the amount of any reagent that has been drawn into the processing vessel falls short of that level, the corresponding sensor output may be used to give an aural and/or visual alarm. Then a required amount of the reagent may be added by the supervisor. Also, even if any reagent vessel contains more than the proper amount of a reagent, the level sensor 36 will function to admit only the proper amount of the reagent into the processing vessel, leaving the extra amount in the reagent vessel.

Trouble may occur to the level sensor 36, and a reagent may overflow from the processing vessel 20. The overflow vessel 76 is intended to accommodate such overflowing liquid. Sensing the overflow, the sensor 90 on the overflow vessel 76 sets off an alarm, not shown, and suspends the operation of the apparatus to prevent the influx of the overflowing solution into the pump 30.

Trouble may also occur to the rotary selector valve assembly 26, resulting in overflow from some reagent vessel 24 into the overflow vessel 58. Then the sensor 60 on this overflow vessel will respond similarly. Such quick detection of, and coping with, overflows is essential to prevent damage to the specimen or specimens being processed and to the apparatus.

A further important feature of the invention resides in the exhaust scrubber 68 which filters and renders innocous all the harmful gases emitted by the reagents in use, prior to release to atmosphere. The exhaust scrubber treats the exhaust gases in two steps, first by water and then by activated carbon. As is well known, the ability of activated carbon to adsorb gas molecules deteriorates at high gas temperatures. Some of the reagents are used at elevated temperatures as aforesaid, and the noxious gases given off by these reagents also have high temperatures as they enter the exhaust scrubber 68. Should they be introduced directly into the adsorbent vessel 100, the hot gases would not be sufficiently adsorbed by the activated carbon.

Thus the exhaust scrubber 68 has the water vessel 98 for pretreating the exhaust gases with water prior to introduction into the adsorbent vessel 100. The water contained in this water vessel serves not only to cool the exhaust gases but also to cause dissolution of water-soluble gases such as that of alcohol.

Figure 3:
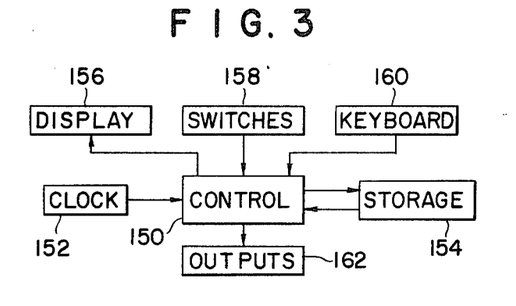
FIG. 3 is a block diagram of control means for the apparatus of FIG. 2.

FIG. 3 block-diagrammatically illustrates a control system designed to automate the apparatus of FIG. 2. A control section 150 consists essentially of a microprocessor for performing various control functions and arithmetic operations. A clock 152, a timepiece, is electrically connected to the microprocessor to enable the latter to ascertain time. A storage device 154 holds in storage the data concerning the various conditions of specimen processing as determined and input by the operator. The processing conditions include, for example, the period during which the specimen or specimens are to be held immersed in each reagent, the need for heating the processing vessel during treatment with each reagent, and the moment of time when the full processing of the specimen or specimens is expected to come to an end.

A display 156 can be of conventional design capable of visually exhibiting information such as the moment of time at which the apparatus is to be set into operation. Control switches generally indicated by the numeral 158 include a start switch and other manual switches for operating the apparatus, all connected to the control section 150. A keyboard 160 is used for inputting the noted processing conditions to the storage device 154 via the control section 150. An output section 162 produces outputs for controlling the valve-actuating motor and solenoids and other electrical parts of the apparatus as dictated by the control section 150.

The control system of FIG. 3 is particularly notable for its abilities to compute the moment of time when the apparatus should be set into operation to complete the processing of the specimen or specimens at an expected moment of time, and to start the operation of the apparatus at the computed moment. For the computation of the starting moment the control section 150 must of course be supplied with data concerning the periods required for various operations involved in the full processing of the specimen or specimens. These periods include:

1. the period of immersion of the specimen or specimens in each reagent in the processing vessel;
2. the period of change from one reagent to another;
3. the period for the rotary selector valve to shift from one inlet port to another; and
4. the period for the processing vessel to be heated to a predetermined temperature as required.

The immersion periods are determined empirically and are input to the storage device 154 from the keyboard 160. The other three periods are ascertained experimentally for each particular apparatus. The period of change from one reagent to another may usually be approximately three minutes, and the period for the rotary selector valve to shift from one inlet port to another may be approximately two seconds.

Receiving from the storage device 154 the data concerning the above periods of time and the moment of time when the apparatus is expected to complete the processing of the specimen or specimens, the microprocessor of the control section 150 computes, backwardly from the expected ending moment, the moment when the apparatus should start the specimen processing. The thus computed starting moment is digitally exhibited on the display 156. Thereafter the microprocessor keeps "watching" the clock 152, sets the apparatus into operation at the computed starting moment, and controls the apparatus so as to cause same to complete operation at the expected moment.

Possibly, the computed starting moment may be earlier than the moment the computation was made, so that the apparatus cannot possibly be started to complete operation at the expected moment. In that case the microprocessor will cause the display 156 to exhibit an indication to that effect.

Figure 4:
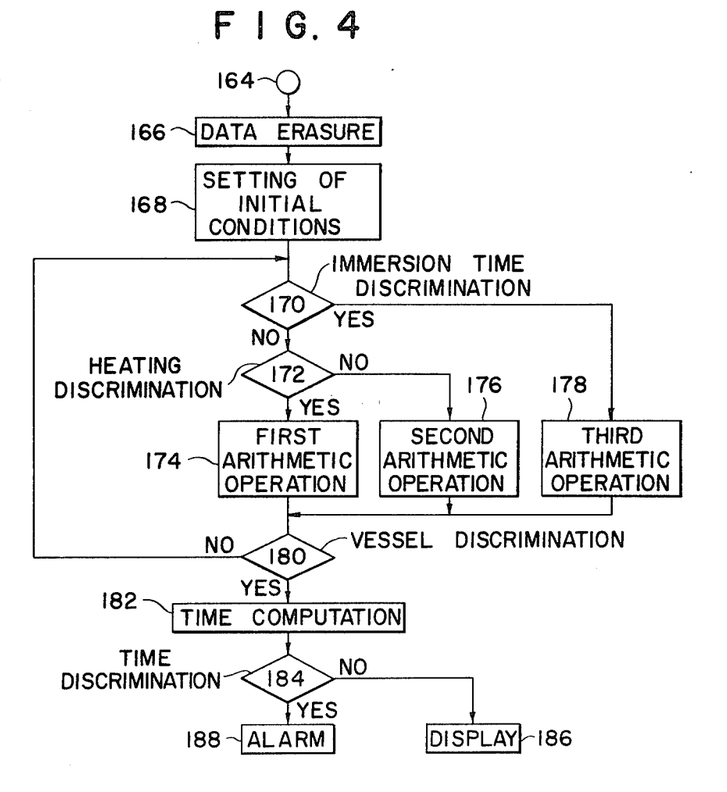
FIG. 4 is a flow chart explanatory of the operation of the control means of FIG. 3.

A study of the FIG. 4 flow chart will make it easier to understand the process of the above computation. As the start switch 164, one of the control switches 158 of FIG. 3, is activated, the data concerning the ending moment of the preceding processing operation are canceled at a block 166 from the storage device 154. Then, at a block 168, the period for the rotary selector valve to communicate the first reagent vessel with the processing vessel and the period of reagent supply from the first reagent vessel are made ready to be added to all the other processing time.

The output from the block 168 is directed into the next block 170, which puts out a YES or NO output depending upon whether the specimen or specimens are to be immersed in a reagent from each reagent vessel for a certain length of time or not, that is, whether the specimen or specimens are to be treated with each reagent or not. The output from the block 170 is NO if each reagent vessel under consideration is to be used.

The NO output is directed into the next block 172. This stage also produces a YES or NO output depending upon whether or not the processing vessel and other pertinent parts of the apparatus are to be heated in the use of the reagent from each reagent vessel. The output is YES if such parts of the apparatus are to be heated.

The YES output from the block 172 enters a first arithmetic operation block 174 where, for each reagent vessel, the period of the shifting of the rotary selector valve, the period of reagent change, the period of heating the required parts of the apparatus to a required temperature, and the period of specimen immersion in the reagent are summed up. This sum is further added at the same stage to the previously calculated sum of like periods for each preceding reagent vessel.

If it is unnecessary to heat the processing vessel and other parts of the apparatus during specimen treatment with the reagent from each reagent vessel, then the block 172 delivers a NO output to a second arithmetic operation block 176. At this stage there is calculated for each reagent vessel the sum of the period of the shifting of the rotary selector valve, the period of reagent change, and the period of specimen immersion. This sum is likewise added to the previously calculated sum of like periods for each preceding reagent vessel.

If a reagent in any reagent vessel is unnecessary for the processing of the particular specimen or specimens in the processing vessel, the immersion time discrimination block 170 delivers a YES output to a third arithmetic operation block 178. At this stage the period of the shifting of the rotary selector valve is added to the sum of like periods for the preceding reagent vessels.

The outputs from the first second and third arithmetic operation blocks 174, 176 and 178 are all input to a vessel discrimination block 180. This stage is intended to check if the computations of the operating periods have been made for all the reagent vessels. A NO output is applied to the immersion time discrimination block 170 if there is a remaining reagent vessel or vessels. Upon completion of the computations for all the reagent vessels, the vessel discrimination block 180 delivers a YES output to the subsequent time computation block 182. It is this stage that computes the starting moment of specimen processing.

The signal representative of the computed starting moment is fed into a time discrimination block 184, where it is examined if the computed starting moment is already past or not. If not, a NO output is applied to a display block 186 for the exhibition of the computed starting moment on the display 156 of FIG. 3. If the starting moment is past, on the other hand, then the time discrimination block 184 applies a YES output to an alarm block 188 to give a visual and/or aural alarm.

Thus the control system of FIGS. 3 and 4 automatically computes the moment of time when the appartus of FIG. 2 must start operation to complete the processing of any desired biological specimen at an expected moment of time, and actually sets the apparatus into operation at the computed starting moment. It is possible in this manner to preclude the possibility of erroneously completing the paraffining of the specimen at a time when no supervisor is present, and of so ruining the specimen.

Figure 5:
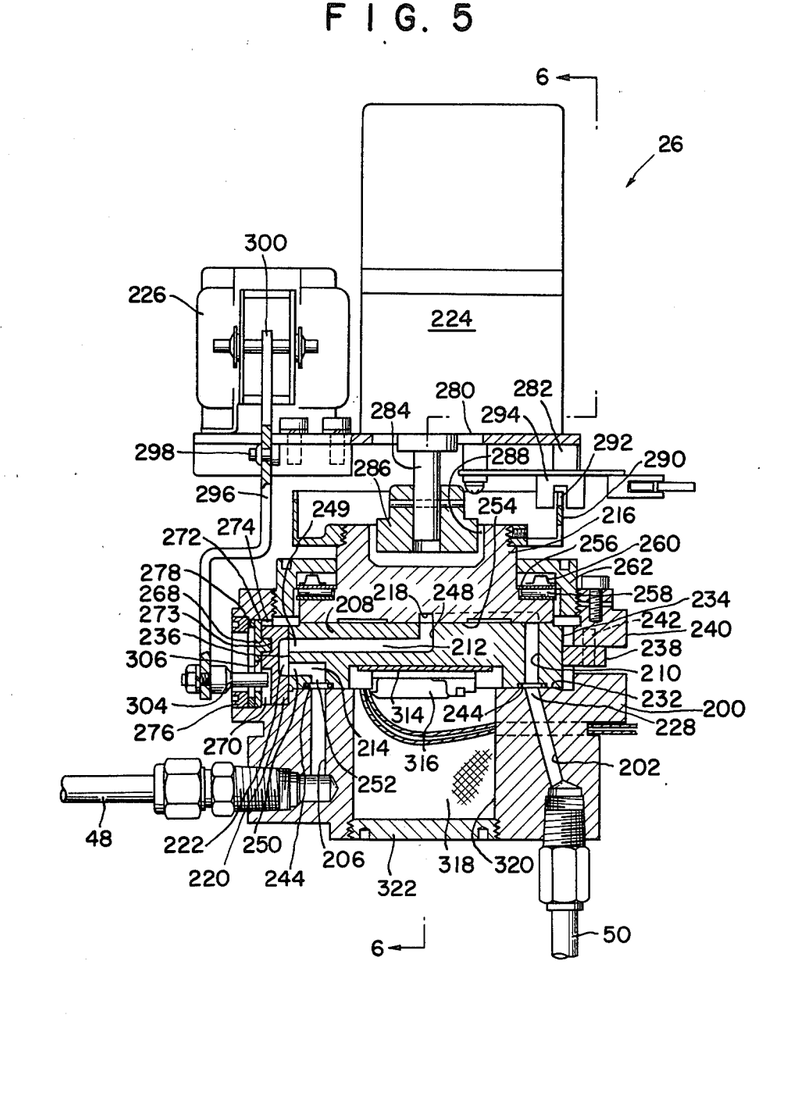
FIG. 5 is a vertical section, partly in elevation, through the rotary selector valve assembly in the apparatus of FIG. 2.
Figure 6:
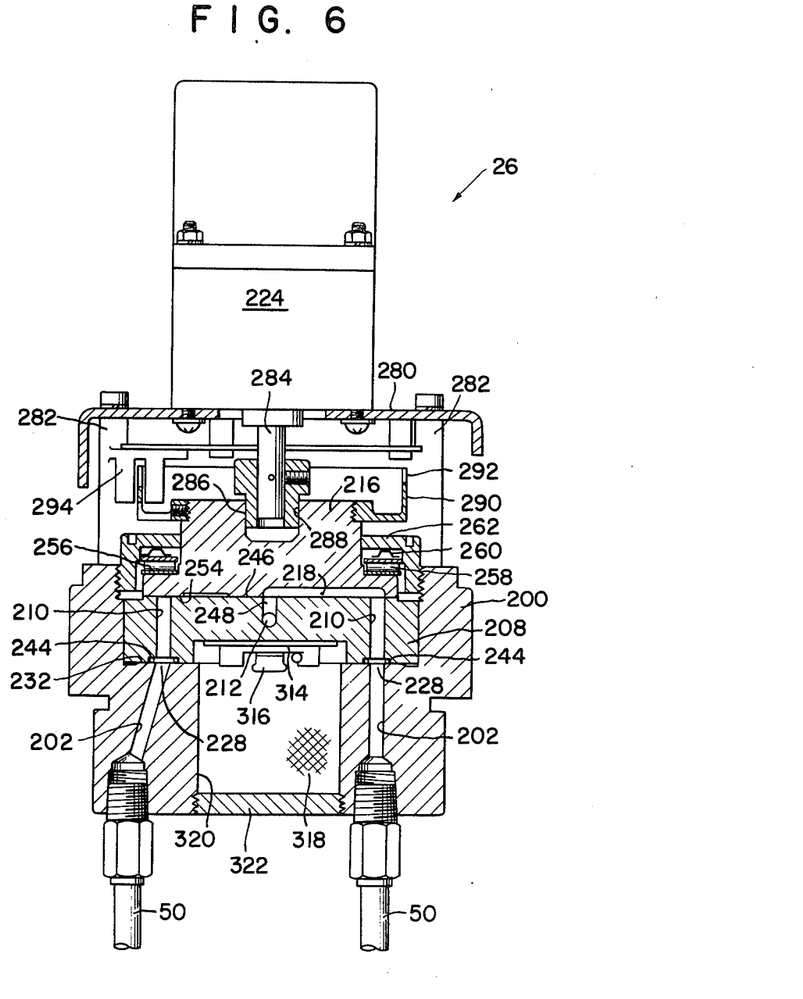
FIG. 6 is also a vertical section, partly in elevation, through the rotary selector valve assembly, the section being taken along the line 6—6 of FIG. 5.
Figure 7:
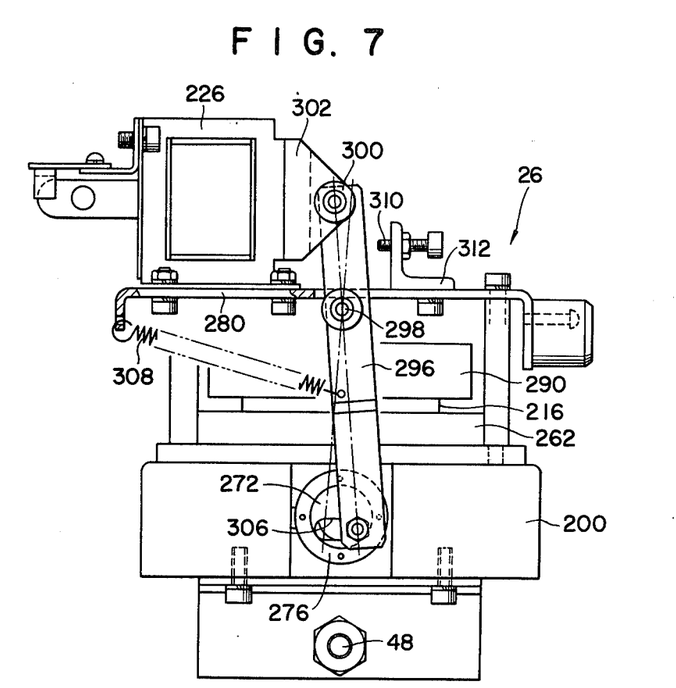
FIG. 7 is a left hand side elevation of the rotary selector valve assembly of FIG. 5.

FIGS. 5 to 11 are detailed representations of a preferred form of the rotary selector valve assembly 26 in the FIG. 2. With reference directed primarily to FIGS. 5, 6 and 7, the rotary selector valve assembly 26 broadly comprises:

1. a valve housing 200 having formed therein a plurality of inlet passages 202 in communication with the respective reagent vessels 24, FIG. 2, via the conduit 50, and an outlet passage 206 in communication with the processing vessel 20, FIG. 2, via the conduit 48;

2. a valve seat 208 fixedly mounted in the valve housing 200 and having formed therein first control passages 210 in constant communication with the respective inlet passages 202 in the valve housing, a second control passage 212, and third control passage 214;

3. a selector valve member 216 rotatably mounted on the valve seat 208 and having formed therein a selector passage 218 for successively communicating the first control passages 210 in the valve seat 208 with the second control passage 212 therein:

4. a gate valve member 220 pivotally mounted to the valve seat 208 and having formed therein a gate passage 222 for the on-off control of communication between the second 212 and third 214 control passages in the valve seat;

5. a motor drive unit 224 for incrementally revolving the selector valve member 216 relative to the valve seat 208; and 6. a solenoid assembly 226 for pivoting the gate valve member 220 relative to the valve seat 208.

Figure 8:
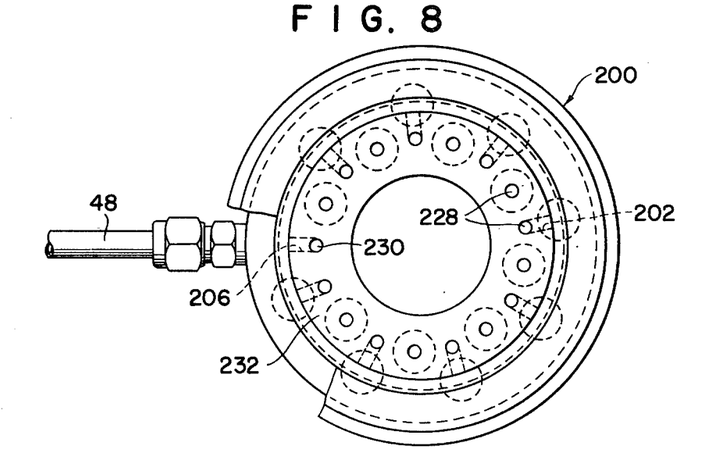
FIG. 8 is a top plan view of the valve housing of the rotary selector valve assembly.

The valve housing 200 is made of steel. The inlet 202 and outlet 206 passages in the valve housing extend substantially vertically therethrough. The top ends 228 of the inlet passages 202 and the top end 203 of the outlet passage 206 are all located in an annular inside ledge 232 of the valve housing 200. FIG. 8 shows that all these top ends 228 and 230 of the passages are in annular arrangement, although the top end 230 of the outlet passage could be disposed elsewhere on the ledge 232. The other ends of the inlet passages 202 are all formed in the bottom surface of the valve housing 200 whereas the other end of the outlet passage 206 is formed in the lateral surface of the valve housing. Some or all of these ends of the inlet passages, however, could also be formed in the lateral surface of the valve housing.

Made of a ceramic such as that of alumina, the valve seat 208 is in the form of a disc of appropriate thickness, fixedly mounted on the annular inside ledge 232 of the valve housing 200. As seen in both FIGS. 5 and 9, the valve seat 208 is recessed in two diametrically opposed positions on its circumference to provide two flat surfaces 234 and 236. Held against the flat 234 is a retainer bar 238 inserted into the valve housing 200 through a slot 240 formed therein and bolted or screwed at 242 to the valve housing. The fixed retainer bar 238 serves the purpose of locking the valve seat 208 against angular displacement relative to the valve housing 200. The other flat 236 serves as a contact surface for relative sliding contact with the gate valve member 220 to be referred to presently.

Figure 9:
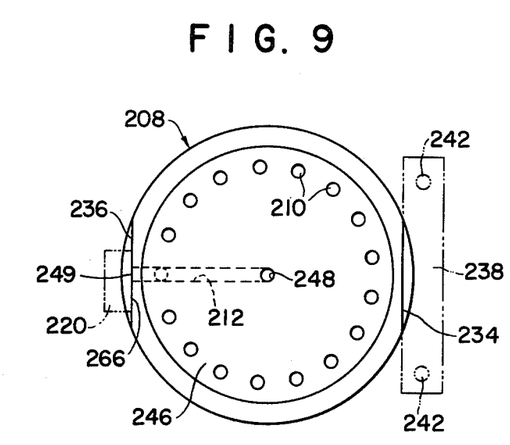
FIG. 9 is a top plan view of the valve seat of the rotary selector valve assembly.

It will be observed from FIGS. 5, 6 and 9 that the first control passages 210 in the valve seat 208 extend vertically therethrough and in annular arrangement. These first control passages are in register with the top ends 228 of the inlet passages 202 in the valve housing 200 and so in constant communication with the respective inlet passages. O-ring seals 244 are installed at the junctions between the inlet passages 202 and the first control passages 210 to assure fluid-tight communication therebetween. The top ends of the first control passages are arranged annularly on the flat top surface 246 of the valve seat 208, which is intended for relative sliding contact with the selector valve member 216. This surface 246 will hereinafter be referred to as the first contact surface of the valve seat, and the aforesaid flat 236 as the second contact surface.

Extending radially of the valve seat 208, the second control passage 212 has one end 248 disposed centrally on the first contact surface 246 with respect to the annularly arranged top ends of the first control passages 210, and another end 249 formed in the second contact surface 236. The third control passage 214 has one end 250 in the second contact surface 236 and another end 252 formed in the bottom surface of the valve seat so as to be in register with the outlet passage 206 in the valve housing 200.

Also of ceramic material, the selector valve member 216 is in the shape of a stepped cylinder, having a flat bottom surface 254 slidably held against the first contact surface 246 of the valve seat 208. The opposed surfaces 246 and 254 of the valve seat and the selector valve member are both machined to a mirrorlike finish for nonleaking contact with each other, even without a packing.

The selector valve member 216 has an annular shoulder 256 on which there are mounted a needle thrust bearing 258 and, thereon, a corrugated spring washer 260. An annular valve cover 262 is rotatably fitted over the reduced diameter portion of the selector valve member 216 and screwed into the valve housing 200, thereby holding the selector valve member against the valve seat 208 via the thrust bearing 258 and spring washer 260. Thus rotatably mounted and retained in position, the selector valve member 216 is in axial alignment with the valve seat 208, with the axis passing the end 248 of the second control passage 212 in the valve seat.

Figure 10:
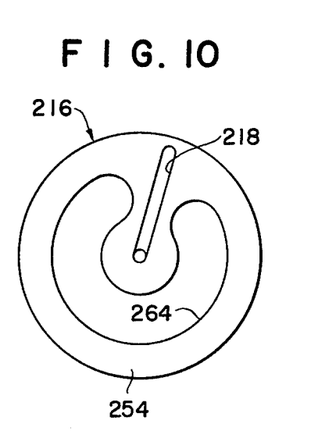
FIG. 10 is a bottom plan view of the selector valve member of the rotary selector valve assembly.

FIG. 10 best reveals the bottom surface 254 of the selector valve member 216. Formed radially therein, the selector passage 218 has one end in a position of register with the first control passages 210 in the valve seat 208, and another end disposed centrally for constant communication with the second control passage 212 in the valve seat. It is thus seen that with the stepwise revolution of the selector valve member relative to the valve seat, the selector passage 218 can communicate the successive first control passages 210 with the second control passage 212. A recess 264 is provided for the reduction of the surface area of the selector valve member for sliding contact with the valve seat with minimal frictional resistance.

Figure 11:
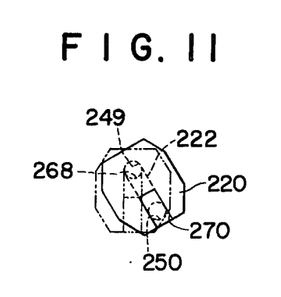
FIG. 11 is a side elevation of the gate valve member of the rotary selector valve assembly.

With reference again to FIGS. 5 and 9 and to FIG. 11, the gate valve member 220 is of generally flat, polygonal shape and is also made of ceramic material. The member has a flat contact surface 266, FIG. 9, slidably held against the second contact surface 236 of the valve set 208. Both of these contact surfaces 236 and 266 are machined to a mirrorlike finish for nonleaking contact with each other. The noted gate passage 222 is formed in this contact surface 266 of the gate valve member, for placing the end 249 of the second control passage 212 in the valve seat 208 in and out of communication with the end 250 of the third control passage 214 in the valve seat.

In the opposite surface of the gate valve member 220 there are formed a circular depression 268 and a groove 270. The depression 268 lies in a position corresponding to that end of the gate passage 222 which is open to the second control passage 212 in the valve seat 208. The groove 270 extends along a line passing the depression 268. Held against this surface of the gate valve member 220 is a holder plate 272 having a pivot 273 projecting therefrom and rotatably fitted in the depression 268 in the gate valve member.

The valve housing 200 has formed therein a mounting hole 274 through which the gate valve member 220 and the holder plate 272 are inserted and mounted in the illustrated working positions. An annular retainer 276 is threadedly engaged in the mounting hole 274 for urging the gate valve member 220 against the valve seat 208 via the holder plate 272 and a corrugated spring washer 278.

The motor drive unit 224 and the solenoid assembly 226 are both positioned on a mount 280 supported on the valve housing 200 via columns 282. The output shaft 284 of the motor drive unit has a key 286 fixedly mounted thereon. This key is closely fitted in a keyway 288 formed in the top end of the selector valve member 216 to impart the rotation of the motor output shaft to the selector valve member. A short, cylindrical wall 290 is rigidly and concentrically mounted to the selector valve member 216 for joint rotation therewith. Disposed astride the top edge of the rotary wall 290, which is slitted as at 292, is a photoelectric switch assembly 294 which is also supported by the mount 280. The photoelectric switch assembly 294 coacts with the slitted rotary wall 290 in the known manner to make the start-stop control of the motor drive unit 224.

FIGS. 5 and 7 clearly illustrate the solenoid assembly 226 and the associated drive linkage to the gate valve member 220. A lever 296 is medially pivoted at a pin 298 on the mount 280. One end of this lever is knucle-jointed at the position 300 to the plunger 302 of the solenoid assembly 226. The other end of the lever rigidly carries a pin 304 extending right-angularly therefrom through a slot 306 in the holder plate 272 and slidably engaged in the groove 270 in the gate valve member 220. A return spring 308 is provided between the mount 280 and lever 296. An adjustable stop 310 is mounted via a lug 312 on the mount 280 for limiting the counterclockwise motion, as view in FIG. 7, of the lever 296.

In FIGS. 5 and 6 is seen an electric heater 314 having a thermostat 316 and mounted on the underside of the valve seat 208 for heating at least those parts of the valve assembly which define the reagent passages. A suitable heat insulator 318 is packed in a hollow 320 created centrally in the valve housing 200 and closed by a threaded cap 322.

In the operation of the rotary selector valve assembly 26, for the delivery of a reagent from one of the reagent vessels to the processing vessel, the motor drive unit 224 may be energized to revolve the selector valve member 216 through an angle necessary to position the outer extremity of the selector passage 218 in register with that one of the first control passages 210 in the valve seat 208 which is in communication with the desired reagent vessel. The solenoid assembly 226 is also energized to cause the lever 296 to turn in a counterclockwise direction, as viewed in FIG. 7, against the bias of the return spring 308. The lever 296 acts via the pin 304 on the gate valve member 220, causing same to turn in the same direction about the pivot 273 to the position depicted in FIG. 11. Now the gate passage 222 in the gate valve member communicates the second control passage 212 in the valve seat 208 with the third control passage 214 therein.

Thus, upon evacuation of the processing vessel by the pump, the desired reagent will be drawn into the processing vessel, as has been explained in connection with FIG. 2. Providing the flow path of the reagent from the reagent vessel to the processing vessel are the conduit 50, one of the inlet passages 202 in the valve housing 200, one of the first control passages 210 in the valve seat 208, the selector passage 218 in the selector valve member 216, the second control passage 212 in the valve seat, the gate passage 222 in the gate valve member 220, the third control passage 214 in the valve seat, the outlet passage 206 in the valve housing, and the conduit 48.

Upon delivery of the required amount of the reagent into the processing vessel, the solenoid assembly 226 is automatically deenergized, as has been explained, to allow the lever 296 to pivot in a clockwise direction, as viewed in FIG. 7, by the force of the return spring 308. Thereupon the gate valve member 220 is pivoted in the same direction to block communication between the second 212 and third 214 control passages in the valve seat 208. Thus is the reagent held contained in the processing vessel.

After specimen immersion in the reagent for a prescribed length of time, the solenoid assembly 226 is reenergized to cause the gate valve member 220 to reestablish communication between the second 212 and third 214 control passages in the valve seat 208. Upon introduction of atmospheric air or pressurized gas into the processing vessel the reagent flows therefrom back to the initial reagent vessel via the rotary selector valve assembly 26.

Then the motor drive unit 224 is reenergized to cause the selector valve member 216 to place the next reagent vessel in communication with the second control passage 212 in the valve seat 208. Thereafter the above cycle of operation is repeated to treat the specimen or specimens with the successive reagents.

The use of ceramics for the valve seat 208, selector valve member 216 and gate valve member 220 offers several advantages. The ceramic-made valve seat and selector and gate valve members are sufficiently rigid to withstand damage from solids such as fragments of tissue, bones and hair that may find their way into the reagents from the biological specimen or specimens being processed. Further, since the contact surfaces of these ceramic members are machined to a mirrorlike finish for nonleaking contact with each other, no sealing means are necessary. The use of rubber packings or the like is objectionable because they are susceptible to ready wear and aging, giving rise to the possibility of reagent leakage. Also the foreign matter in the reagents may easily bite into such elastic packings, again possibly causing leakage. Ceramics are excellent in both heat conductivity and heat resistance, so that the ceramic valve seat and valve members can be readily heated to any required temperature for the flow of molten paraffin and other reagents. Further there is no likelihood of seizure taking place between the relatively sliding surfaces of these parts. The resistance of ceramics to chemicals is also favorable.

It will also be seen that the rotary selector valve assembly 26 is held closed by the gate valve member 220, with the solenoid assembly 226 held deenergized, except during the flow of each reagent to and from the processing vessel. Consequently, even if the reagent in the processing vessel is subjected to atmospheric pressure because of a power failure, the reagent is not to be drained therefrom.

All in all, the rotary selector valve assembly 26 of the above construction is durable, positive in operation, and easy of manufacture.

Figure 12:
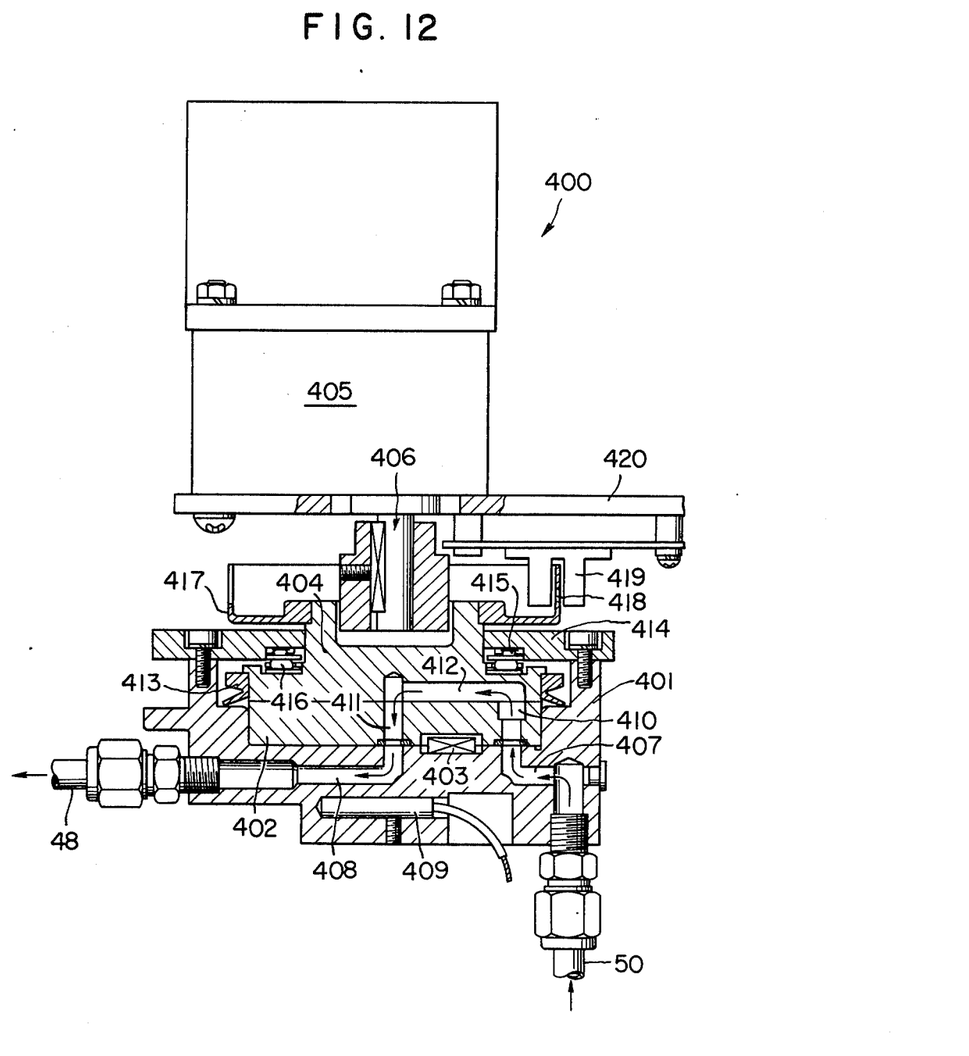
FIG. 12 is a vertical section of another rotary selector valve assembly.

FIG. 12 shows another embodiment of the rotary selector valve 26. In FIG. 12, a rotary selector valve 400 has a housing 401 in which a valve seat 402 is fixed by a key 403. On the valve seat 402 is rotatably mounted a selector valve member 404 similar to the above mentioned selector valve member 216. The selector valve member 404 is rotated by a motor drive unit 405 via a connecting mechanism 406.

In the housing 401 are provided a plurality of inlet passages 407 connected to the conduits 50, a outlet passage 408 connected to the conduit 48 and a heater 409. The valve seat 402 has a plurality of first control passages 410 in register with the respective inlet passage 407 and a second control passage 411 in register with the outlet passage 408. The second control passage 411 is provided in the center of the valve seat 402.

In the lower surface of the selector valve member 404 is formed a selector passage 412 extending radially and having an inner end in constant register with the second control passage 411, and an outer end in selective register with each of the inlet passages 407. There is provided a ring 413 for preventing the leakage of the fluid on the peripheral surface of selector valve member 404.

The housing 401 is covered with a plate 414 at the upper face which supports rotatably via a spring washer 415 and a thrust bearing 416.

To the upper part of the selector valve member 404 is fixed a slitted cylindrical wall 417 having a plurality of slits 418 at predetermined intervals which coact with a photoelectric sensor 419 hung from a mount 420. The photoelectric sensor 418 operates the motor drive unit 405 is such a manner that it stops the unit 405 when the selector valve member 404 is rotated so that the outer end of the selector passage 412 is positioned between two adjoining first control passages 410 thereby to disconnect the passage 412 from the passage 410 and positioned in register with each of the first control passages 410 thereby to selectively connect the passage 412 to each of the first passages 410.

The rotary selector valve 26 has no such a gate valve mechanism corresponding to the above gate valve member 220, the solenoid assembly 226, etc., accordingly the construction of this valve 400 is remarkably simplified.

What is claimed is:

1. An apparatus for automatically pretreating biological specimens and embedding same in paraffin or like substance for the preparation of blocks to be cut into sections for microscopical examination, said apparatus comprising:
    (a) a processing vessel for receiving a biological specimen to be processed into a block, the processing vessel being openably closed hermetically;
    (b) a plurality of reagent vessels for containing reagents for processing the biological specimen in the processing vessel;
    (c) selector valve means for placing selectively the reagent vessels in and out of communication with the processing vessel in a prescribed sequence;
    (d) an air pump for evacuating the processing vessel in order to cause introduction therein of the successive reagents from the reagent vessel via the selector valve means, and for delivering gas under pressure into the processing vessel in order to discharge the reagents therefrom back into the reagent vessels;
    (e) directional control valve means for selectively causing the pump to evacuate and pressurize the processing vessel;
    (f) a level sensor on the processing vessel for setting the pump out of operation and causing the selector valve means to block communication between the processing vessel and one of the reagent vessels when the reagent from the latter is drawn into the evacuated processing vessel to a predetermined level;
    (g) pressure switch means responsive to the pressure of the pressurized gas delivered from the pump into the processing vessel in order to cause the selector valve means to reestablish communication between the processing vessel and one of the reagent vessel from which the reagent has been drawn into the processing vessel, the pressure switch means being further responsive to a pressure drop upon complete discharge of the reagent from the processing vessel in order to set the pump out of operation and to cause the selector valve means to communicate the processing vessel with the next reagent vessel;
    (h) overflow vessel means for receiving any reagent overflowing from the processing vessel and at least some of the reagent vessels, at least one overflow vessel means being located on a line between the air pump and the processing vessel; and
    (i) scrubbing means for scrubbing the toxic gases emitted in the apparatus prior to release to atmosphere, said scrubbing means comprising a hermetically closed water vessel for containing water and an absorbent vessel for containing an absorbent, said water vessel being connected to the headspace of the processing vessel through the overflow vessel means provided between the air pump and the processing vessel and to some of the reagent vessels, the absorbent vessel being in constant communication with the headspace of the water vessel and with atmosphere.

2. An apparatus according to claim 1, wherein said the overflow vessel means have sensors for sensing the overflow from the processing vessel and some of the reagent vessels, respectively.

3. An apparatus according to claim 1, wherein some of the reagent vessels are housed in an oven.

4. An apparatus according to claim 1, wherein the reagent vessels are disposed lower than the processing vessel, and wherein the apparatus further comprises means for the admission of scrubbed atmospheric air into the processing vessel for the discharge of the reagent therefrom back into the reagent vessel from which it has been drawn.

5. Apparatus for automatically pretreating biological specimens and embedding same in paraffin or like substance for the preparation of blocks to be cut into sections for microscopical examination, the apparatus comprising:
  (a) a processing vessel for receiving a biological specimen to be processed into a block, the processing vessel being openably closed hermetically;
  (b) a plurality of reagent vessels for containing reagents for processing the biological specimen in the processing vessel;
  (c) selector valve means for placing selectively the reagent vessels in and out of communication with the processing vessel in a prescribed sequence, said selector valve means comprising, (1) a valve housing having formed therein a plurality of inlet passages in communication with the respective reagent vessels and also having formed therein an outlet passage in communication with the processing vessel, (2) a valve seat fixedly mounted in the valve housing and having first and second flat contact surfaces, the valve seat having formed therein a plurality of first control passages and a second control passage and a third control passage, the first control passages having first extremities in constant communication with the respective inlet passages in the valve housing and second extremities arranged annularly in the first contact surface of the valve seat, the second control passage having a first extremity disposed centrally in the first contact surface of the valve seat with respect to the annularly arranged extremities of the first control passages and having a second extremity in the second contact surface of the valve seat, the third control passage having a first extremity in the second contact surface of the valve seat and a second extremity in constant communication with the outlet passage in the valve housing, (3) a selector valve member having a contact surface slidably but fluid-tightly held against the first contact surface of the valve seat, the selector valve member being rotatably relative to the valve seat about an axis passing the first extremity of the second control passage in the valve seat, there being a selector passage formed in the contact surface of the selector valve member for successively placing the second extremities of the first control passages in the valve seat in communication with the first extremity of the second control passage in the valve seat with the rotation of the selector valve member, (4) means for revolving the selector valve member relative to the valve seat, (5) a gate valve member having a contact surface slidably but fluid-tightly held against the second contact surface of the valve seat, the gate valve member being pivotable relative to the valve seat, there being a gate passage formed in the contact surface of the gate valve member for placing the second extremity of the second control passage in the valve seat in and out of communication with the first extremity of the third control passage in the valve seat with the pivotal motion of the gate valve member, and (6) means for pivoting the gate valve member relative to the valve seat, said valve seat the selector valve member and the gate valve member of the selector valve means are all of ceramic material.

6. The apparatus according to claim 5, wherein the revolving means of the selector valve means commprises:
  (a) a mount immovably supported on the valve housing;
  (b) a motor drive unit of the mount; and
  (c) a key fixedly mounted on an output shaft of the motor drive unit and engaged in a keyway formed in the selector valve member.

7. The apparatus according to claim 5, wherein the pivoting means of the selector valve means comprising:
  (a) a mount immovably supported on the valve housing;
  (b) a solenoid assembly on the mount;
  (c) a lever pivotally supported intermediately to its ends on the mount and having one end pivotally coupled to a plunger of the solenoid assembly and the other end operatively coupled to the gate valve member; and
  (d) resilient means acting on the lever to normally hold the gate valve member in a position to block communication between the second and third control passage in the valve seat.

8. The apparatus according to claim 5, wherein the selector valve means further comprises a thermostatically controlled heater for heating the parts having the passages formed therein.

9. Apparatus for automatically pretreating biological specimens and embedding same in paraffin or like substance for the preparation of blocks to be cut into sections for microscopical examination, the apparatus comprising:
  (a) a processing vessel for receiving a biological specimen to be processed into a block, the processing vessel being openly closed hermetically;
  (b) a plurality of reagent vessels for containing reagents for processing the biological specimen in the processing vessel;
  (c) selector valve means for placing selectively the reagent vessels in and out of communication with the processing vessel in a prescribed sequence said selector valve means comprising, (1) a valve housing provided with a plurality of inlet passages in communication with the respective reagent vessels and also provided with an outlet passage in communication with the processing vessel, (2) a valve seat fixedly mounted in the valve housing having a plurality of first control passages in constant register with the inlet passages respectively and a second control passage in the center thereof in constant register with the outlet passage, (3) a selector valve member rotatably mounted on the valve seat and having a selector passage extending radially, the inner end of which is in constant register with the second control passage of the valve seat and the outer end of which is in selective register with the first control passage thereof, (4) driving means for revolving the selector valve member relative to the valve seat, and (5) sensoring means controlling the driving means in such a manner that it stops the driving means when the selector valve member is rotated through a predetermined angle in order to connect the selector passage to each of the first control passage and disconnect the former passage from the latter passage, whereby said valve seat and the selector valve member being of ceramic material.

* * * * *